(12) United States Patent
Duhaylongsod et al.

(10) Patent No.: US 6,241,741 B1
(45) Date of Patent: *Jun. 5, 2001

(54) ANASTOMOSIS DEVICE AND METHOD

(75) Inventors: Francis G. Duhaylongsod, Durham, NC (US); Fritz French, Menlo Park, CA (US)

(73) Assignee: Corvascular Surgical Systems, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/037,113

(22) Filed: Mar. 9, 1998

(51) Int. Cl.$^7$ .................................................. A61B 17/00
(52) U.S. Cl. .............................................................. 606/153
(58) Field of Search .................................. 606/153, 151, 606/108, 194, 198; 604/96, 104–109; 128/898; 623/1, 12

(56) References Cited

U.S. PATENT DOCUMENTS

| | | |
|---|---|---|
| 3,254,650 | 6/1966 | Collito . |
| 3,254,651 | 6/1966 | Collito . |
| 3,519,187 | 7/1970 | Kapitanov et al. . |

(List continued on next page.)

FOREIGN PATENT DOCUMENTS

| | | |
|---|---|---|
| 24 50 877 | 5/1975 | (DE) . |
| 0688544 A2 | 12/1995 | (EP) . |
| 0791332 A1 | 8/1997 | (EP) . |
| WO 95/09584 | 4/1995 | (WO) . |
| WO 96/07355 | 3/1996 | (WO) . |
| WO 96/25897 | 8/1996 | (WO) . |
| PCT/US97/02044 | 8/1997 | (WO) . |
| WO 97/29716 | 8/1997 | (WO) . |
| WO 98/19608 | 5/1998 | (WO) . |
| WO 98/19618 | 5/1998 | (WO) . |
| WO 98/19629 | 5/1998 | (WO) . |

(List continued on next page.)

OTHER PUBLICATIONS

Carter et al., "Direct Nonsuture Coronary Artery Anastomosis in the Dog" *Ann. Surg.*(1958)*148*:212–218.

Coggia et al., "Anastomosis over a stent for heavily calcified arteries"*Ann. Vasc. Surg.* (1995) *9*[suppl]:S39–S44.

Costello et al., "Sutureless end–to–end bowel anastomosis using Nd:YAG and water–soluble intraluminal stent" *Lasers Surg. Med.* (1990) *10*(2):179–184.

(List continued on next page.)

*Primary Examiner*—Gary Jackson
*Assistant Examiner*—Vikki Trinh
(74) *Attorney, Agent, or Firm*—Morrison & Foerster LLP

(57) ABSTRACT

A method for coupling a first vessel and a second vessel in an anastomosis. The method includes providing a first vessel with a fastener coupled thereto, inserting at least a portion of the device into the second vessel with an end portion of the fastener extending generally longitudinally through the second vessel, and radially expanding at least a portion of the fastener to sealingly secure the first vessel to an inner wall of the second vessel. An anastomosis fastener for use in coupling the first and second vessels together is also disclosed. The second vessel has an opening formed in a side wall thereof for insertion of the device. The device includes a tubular member at least a portion thereof being radially expandable. The tubular member is preformed with a bend along its central longitudinal axis so that a portion of the tubular member extends out from the side wall of the second vessel while an end portion of the tubular member extends generally coaxially with the second vessel when the tubular member is inserted in the second vessel. The tubular member is sufficiently rigid to substantially retain the tubular member in its preformed configuration after the tubular member is expanded.

20 Claims, 13 Drawing Sheets

U.S. PATENT DOCUMENTS

| | | |
|---|---|---|
| 3,561,448 | 2/1971 | Peternel . |
| 3,657,744 | 4/1972 | Ersek . |
| 3,683,926 | 8/1972 | Suzuki . |
| 3,774,615 | 11/1973 | Lim et al. . |
| 3,805,793 | 4/1974 | Wright . |
| 4,350,160 | 9/1982 | Kolesov et al. . |
| 4,352,358 | 10/1982 | Angelchik . |
| 4,366,819 | 1/1983 | Kaster . |
| 4,368,736 | 1/1983 | Kaster . |
| 4,523,592 | 6/1985 | Daniel . |
| 4,553,542 | 11/1985 | Schenk et al. . |
| 4,593,693 | 6/1986 | Schenk . |
| 4,596,728 | 6/1986 | Yang et al. . |
| 4,607,637 | 8/1986 | Berggren et al. . |
| 4,624,255 | 11/1986 | Schenck et al. . |
| 4,624,257 | 11/1986 | Berggren et al. . |
| 4,657,019 | 4/1987 | Walsh et al. . |
| 4,665,906 | 5/1987 | Jervis . |
| 4,712,551 | 12/1987 | Rayhanabad . |
| 4,733,665 * | 3/1988 | Palmaz ............................. 604/104 X |
| 4,747,407 | 5/1988 | Liu et al. . |
| 4,776,337 | 10/1988 | Palmaz . |
| 4,787,386 | 11/1988 | Walsh . |
| 4,873,975 | 10/1989 | Walsh et al. . |
| 4,907,591 | 3/1990 | Vasconcellos et al. . |
| 4,917,087 | 4/1990 | Walsh et al. . |
| 4,917,090 | 4/1990 | Berggren et al. . |
| 4,917,091 | 4/1990 | Berggren et al. . |
| 4,917,114 | 4/1990 | Green et al. . |
| 5,100,429 | 3/1992 | Sinofsky et al. . |
| 5,119,983 | 6/1992 | Green et al. . |
| 5,197,978 * | 3/1993 | Hess ......................................... 623/1 |
| 5,199,951 | 4/1993 | Spears . |
| 5,213,580 | 5/1993 | Slepian et al. . |
| 5,336,233 | 8/1994 | Chen . |
| 5,366,462 | 11/1994 | Kaster et al. . |
| 5,410,016 | 4/1995 | Hubbell et al. . |
| 5,443,497 | 8/1995 | Venbrux ................................... 623/1 |
| 5,456,713 | 10/1995 | Maginot . |
| 5,478,354 | 12/1995 | Tovey et al. . |
| 5,503,635 | 4/1996 | Sauer et al. . |
| 5,522,834 | 6/1996 | Fonger et al. . |
| 5,522,881 | 6/1996 | Lentz . |
| 5,527,355 | 6/1996 | Ahn . |
| 5,562,690 | 10/1996 | Green et al. . |
| 5,662,712 | 9/1997 | Pathak et al. . |
| 5,695,504 | 12/1997 | Gifford et al. . |
| 5,698,189 | 12/1997 | Rowe et al. . |
| 5,899,935 * | 5/1999 | Ding ......................................... 623/1 |
| 5,902,332 * | 5/1999 | Schatz ...................................... 623/1 |
| 5,989,276 | 11/1999 | Houser et al. . |

FOREIGN PATENT DOCUMENTS

| | | |
|---|---|---|
| WO 98/19630 | 5/1998 | (WO) . |
| WO 98/19631 | 5/1998 | (WO) . |
| WO 98/19632 | 5/1998 | (WO) . |
| WO 98/19634 | 5/1998 | (WO) . |
| WO 98/19636 | 5/1998 | (WO) . |
| WO 98/55027 | 12/1998 | (WO) . |

OTHER PUBLICATIONS

Detweiler et al., "Sliding, absorbable, reinforced ring and an axially driven stent placement device for sutureless fibrin glue gastrointestinal anastomosis " *J. Invest. Surg.* (1996) *9*(6):495–504 plus Abstract (2 pp.).

Detweiler et al., "Sutureless anastomosis of the small intestines and the colon in pigs using and absorbable intraluminal stent and fibrin glue" *J. Invest. Surg.* (1995) *8*(2): 129–140.

Goetz et al., "Internal Mammary–Coronary Artery Anastomosis: A Nonsuture Method Employing Tantalum Rings" *J. Thorac. Cardio. Surg.* (1961)*41*:378–386.

Hardy, "Non–suture anastomosis: The historical development" *N.Z.J. Surg.* (1990) *60*:625–633.

Jiao et al., "Anastomosis of small artery using ZT medical adhesive and soluble stent" *Chung Hua Cheng Hsing Shao Shang Wai Ko Tsa Chih* (1994) *10*(5):334–336 (English abstract enclosed).

Kamiji et al., "Microvascular anastomosis using polyethlene glycol 4000 and fibrin glue" *British J. Plastic Surg.* (1989) *42*:54–58.

Mikaelsson et al., "Nonsuture end–to–end microvascular anastomosis using intravascular stents"*Ann. Chir. Gynaecol.* (1996) *85*(1):36–39.

Moskovitz et al., "Microvascular anastomoses utilizing new intravascular stents"*Ann. Plast. Surg.* (1994) *32*:612–618.

Rivetti et al., "Initial experience using and intraluminal shunt during revascularization of the beating heart " *Ann. Thorac. Surg.* (1997) *63*:1742–1747.

Robinson et al., "Transient ventricular asystole using adenosine during minimally invasive and open sternotomy coronary artery bypass grafting" *Ann. Thorac. Surg.*(1997)*63*:S30–S34.

Rösch et al., "Experimental intrahepatic portacaval anastomosis: Use of expandable Gianturco stents" *Radiology* (1987) *162*(2):481–485.

Schöb et al., "New anastomosis technique for (laparoscopic) instrumental small–diameter anastomosis" *Surg. Endosc.* (1995) *9*(4):444–449.

Vorwerk et al., "Sutureless vascular end–to–end end–to–side anastomosis: An in vivo test of a percutaneous concept in the animal model" *Rofo Fortschr Geb Rontgenstr Neuen Bildgeb Verfahr* (1997) *167*(1):83–86 (English abstract enclosed).

Wei et al., "The temporary stent technique: an easier method of micro–venous anastomosis " *Br. J. Plast. Surg.* (1992) *35*(1):92–95.

\* cited by examiner

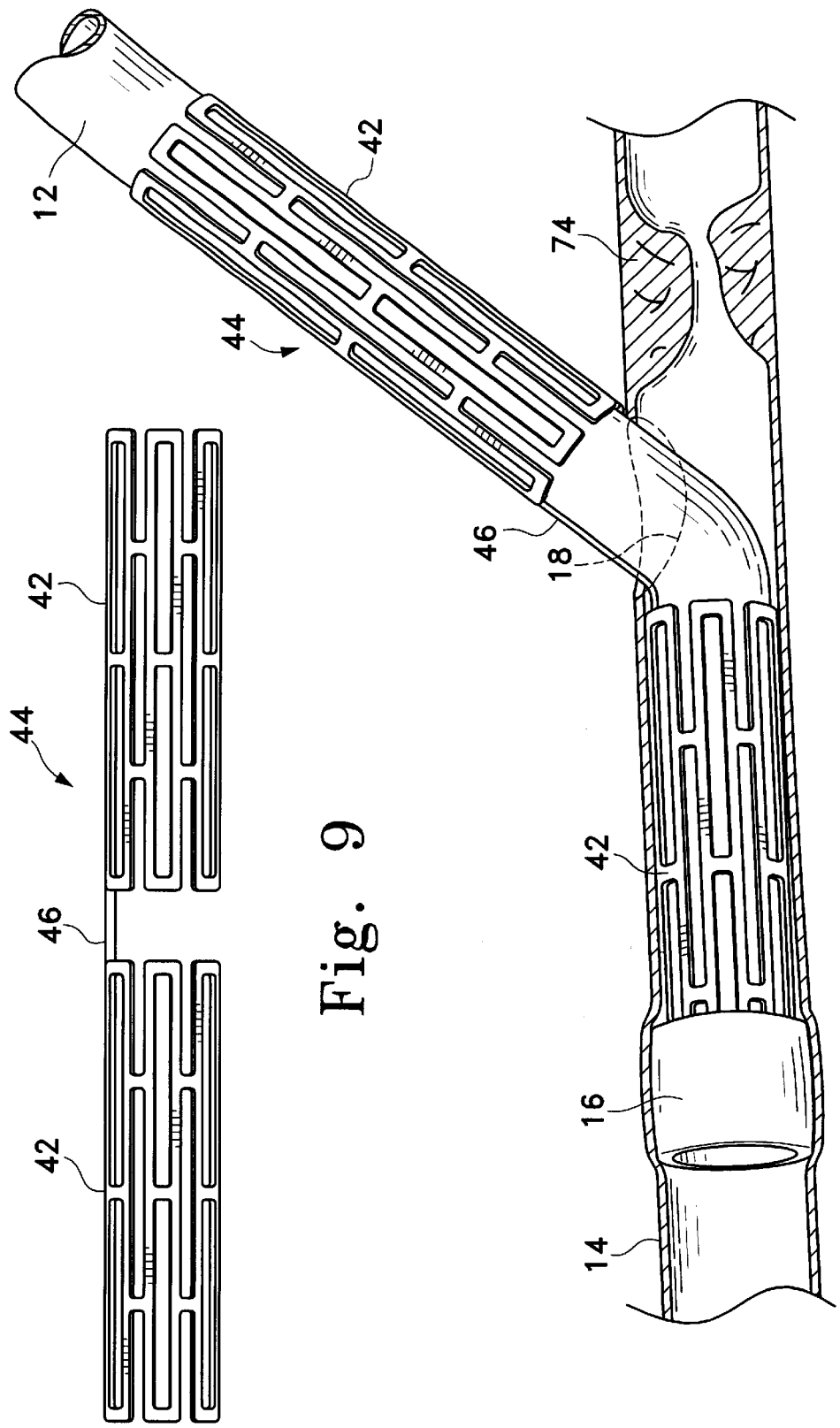

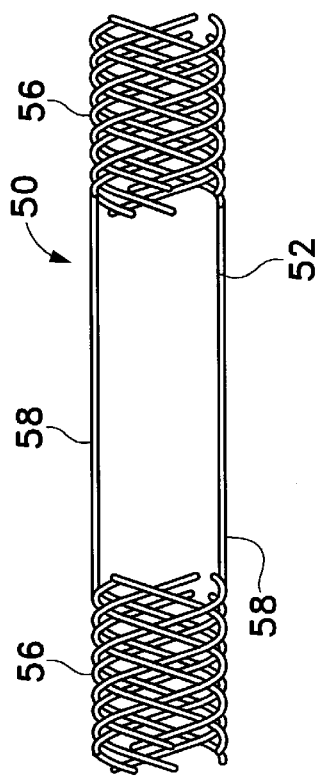
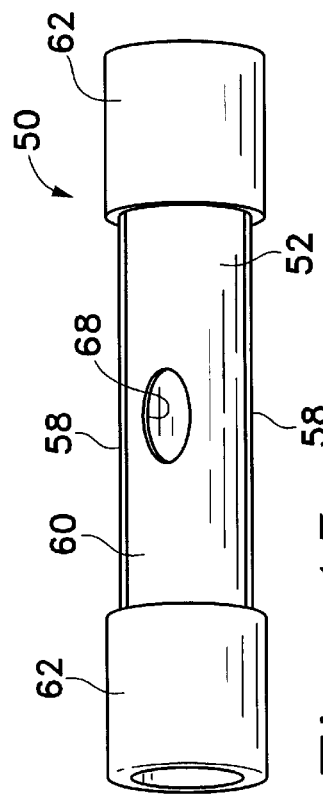
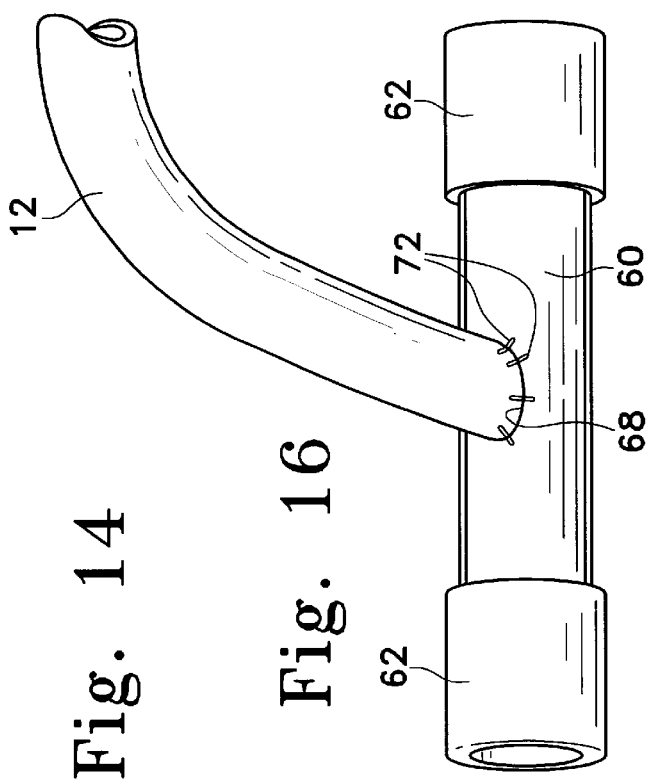
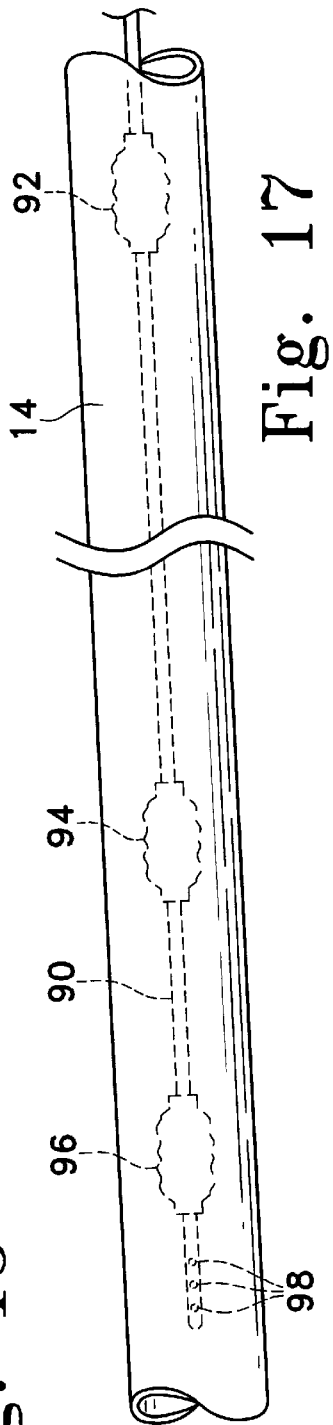

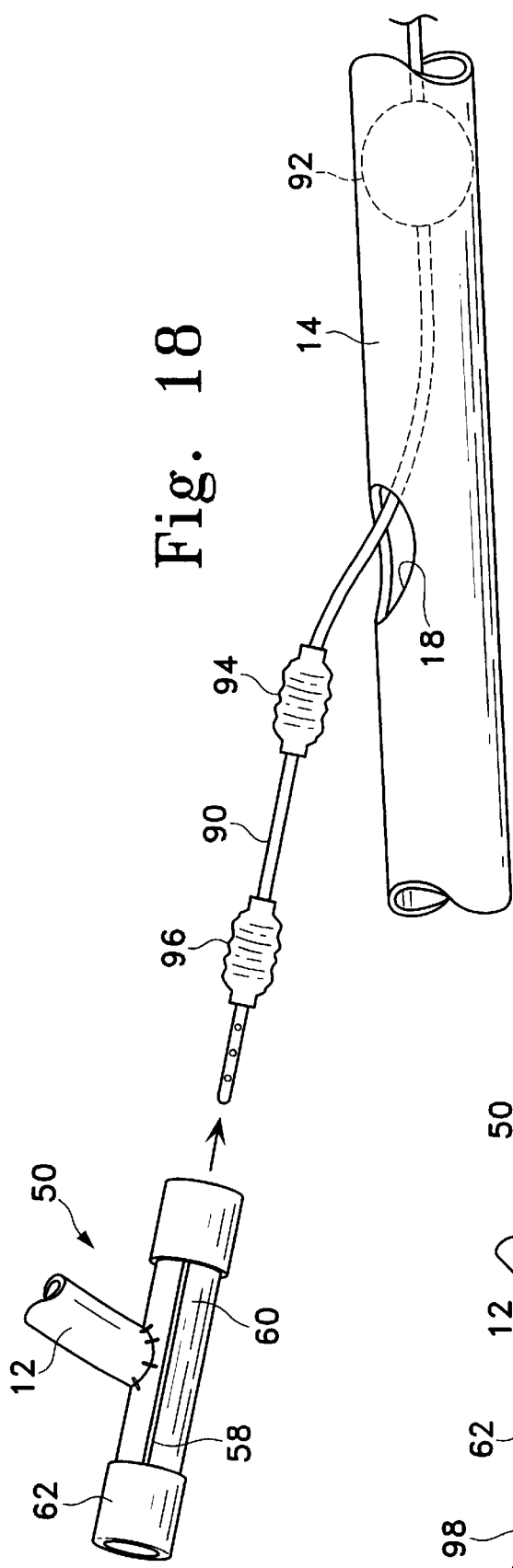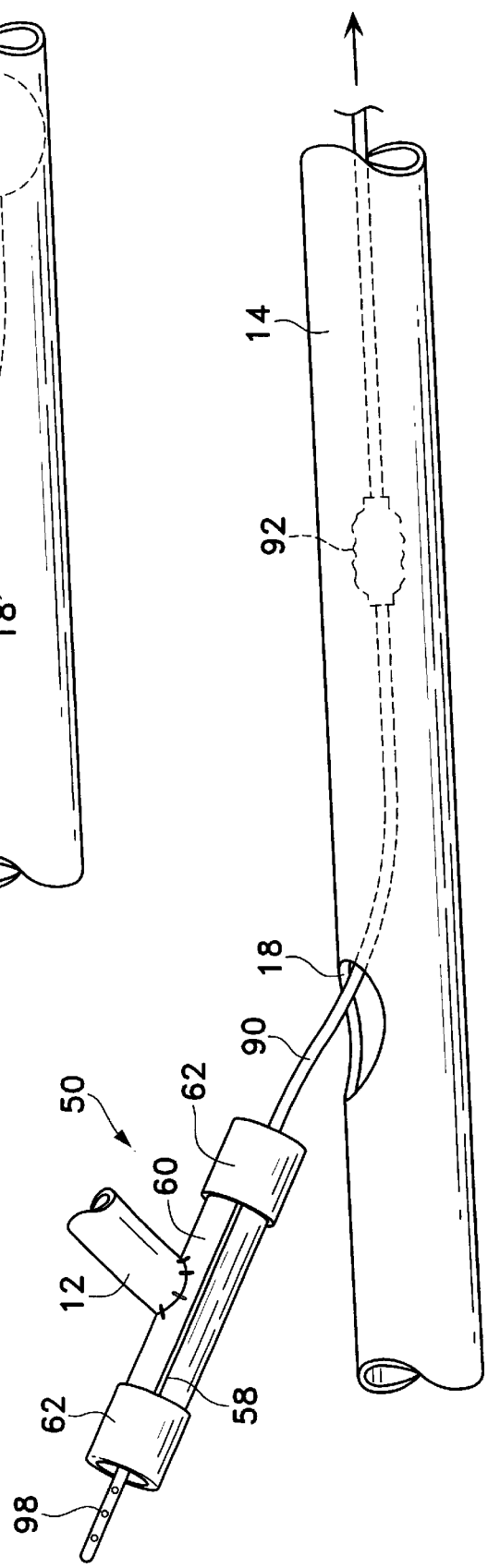

ANASTOMOSIS DEVICE AND METHOD

FIELD OF THE INVENTION

The present invention relates generally to devices and methods for performing a vascular anastomosis and, more particularly, to a device for coupling the end of a vessel, such as a coronary bypass graft, to the side wall of a vessel, such as a coronary artery.

BACKGROUND OF THE INVENTION

A manifestation of coronary artery disease is the build-up of plaque on the inner walls of the coronary arteries, which causes narrowing or complete closure of these arteries, resulting in insufficient blood flow. Surgery to alleviate this problem often involves creating an anastomosis between a blood vessel and a graft vessel to restore a blood flow path to essential tissues.

Current methods available for creating an anastomosis include hand suturing the vessels together. Suturing the anastomosis is time-consuming and often does not provide a leak-free seal. Furthermore, suturing requires the heart to be isolated from the systemic circulation, and the heart must typically be stopped for an extended period of time, so that the anastomosis site on the heart is blood-free and still during the suturing of the anastomosis. Thus, it is desirable to reduce the difficulty of creating the vascular anastomosis and provide a rapid method for making a reliable anastomosis between a graft vessel and artery.

One method available for expediting anastomosis procedures is through the use of anastomosis fittings for joining blood vessels together. These fittings, however, require multiple components which make installation of the fitting difficult and time consuming. Moreover, these fittings expose foreign material of the fittings to the blood flow path within the arteries, which increases the risks of hemolysis and thrombosis.

Another method currently available involves the use of stapling devices. These instruments are not easily adaptable for use in vascular anastomosis. It is often difficult to manipulate these devices through the vessels without inadvertently piercing a side wall of the vessel. In addition to being difficult to operate, these devices often do not provide a reliable leak-free seal.

SUMMARY OF THE INVENTION

The present invention involves improvements to devices and methods for performing vascular anastomoses. The invention facilitates positioning one vessel in the fluid path of another vessel to enhance the fluid flow juncture therebetween. In one aspect of the invention, the two vessels are sealingly secured to one another without the need for sutures.

A method of the present invention is for coupling a first vessel and a second vessel in an anastomosis and generally includes providing a fastener attached to the first vessel, inserting at least a portion of the fastener into an opening formed in a side wall of the second vessel with an end portion of the fastener extending generally longitudinally within the second vessel, and radially expanding at least a portion of the fastener to sealingly secure the first vessel to an inner wall of the second vessel.

According to one aspect of the present invention, the fastener comprises a tubular member at least a portion thereof being radially expandable. The tubular member is preformed with a bend along its central longitudinal axis so that a portion of the tubular member extends out of the side wall of the second vessel while an end portion of the tubular member extends out from the side wall of the second vessel while an end portion of the tubular member extends generally coaxially with the second vessel when the device in inserted in the second vessel. The tubular member is sufficiently rigid to substantially retain the tubular member in its preformed configuration after the tubular member is radially expanded.

In another aspect of the present invention, the first vessel is attached to the tubular member and the tubular member is transformable between a compressed state in which the member has a diameter smaller than the diameter of the second vessel to permit the fastener to move longitudinally within the second vessel, and an expanded state in which at least a portion of the fastener has a diameter at least equal to the diameter of the second vessel to sealingly engage the first vessel with the second vessel.

In yet another aspect of the present invention, the device comprises a tubular member having two expandable end portions and a central portion having a cylindrical member formed of a substantially nonporous material. The cylindrical member has an opening formed in a side wall thereof.

The above is a brief description of some deficiencies in the prior art and advantages of the present invention. Other features, advantages, and embodiments of the invention will be apparent to those skilled in the art from the following description, accompanying drawings and claims.

BRIEF DESCRIPTION OF THE DRAWINGS

FIG. 9 is an elevated view of a second embodiment of an anastomosis device constructed according to the principles of the present invention;

FIG. 10 shows the anastomosis device of FIG. 9 attached to a graft vessel and inserted into an artery;

FIG. 14 is an elevated view of a fourth embodiment of an anastomosis device constructed according to the principles of the present invention;

FIG. 15 is an elevated view of the anastomosis device of FIG. 14 with a vessel inserted therethrough;

FIG. 16 is an elevated view of the anastomosis device of FIG. 15 with a graft vessel connected thereto;

FIG. 17 shows an artery having a balloon catheter inserted therein;

FIG. 18 shows the device of FIG. 16 being placed over the balloon catheter;

FIG. 19 shows the device of FIG. 16 and the balloon catheter being inserted into the artery;

Corresponding reference characters indicate corresponding parts throughout the several views of the drawings.

DESCRIPTION OF THE INVENTION

Figure 1:
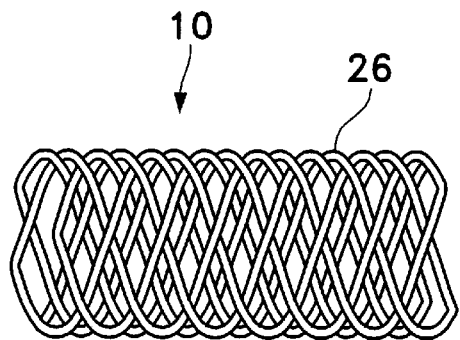
FIG. 1 is an elevated view of an anastomosis device of the present invention.
Figure 2:
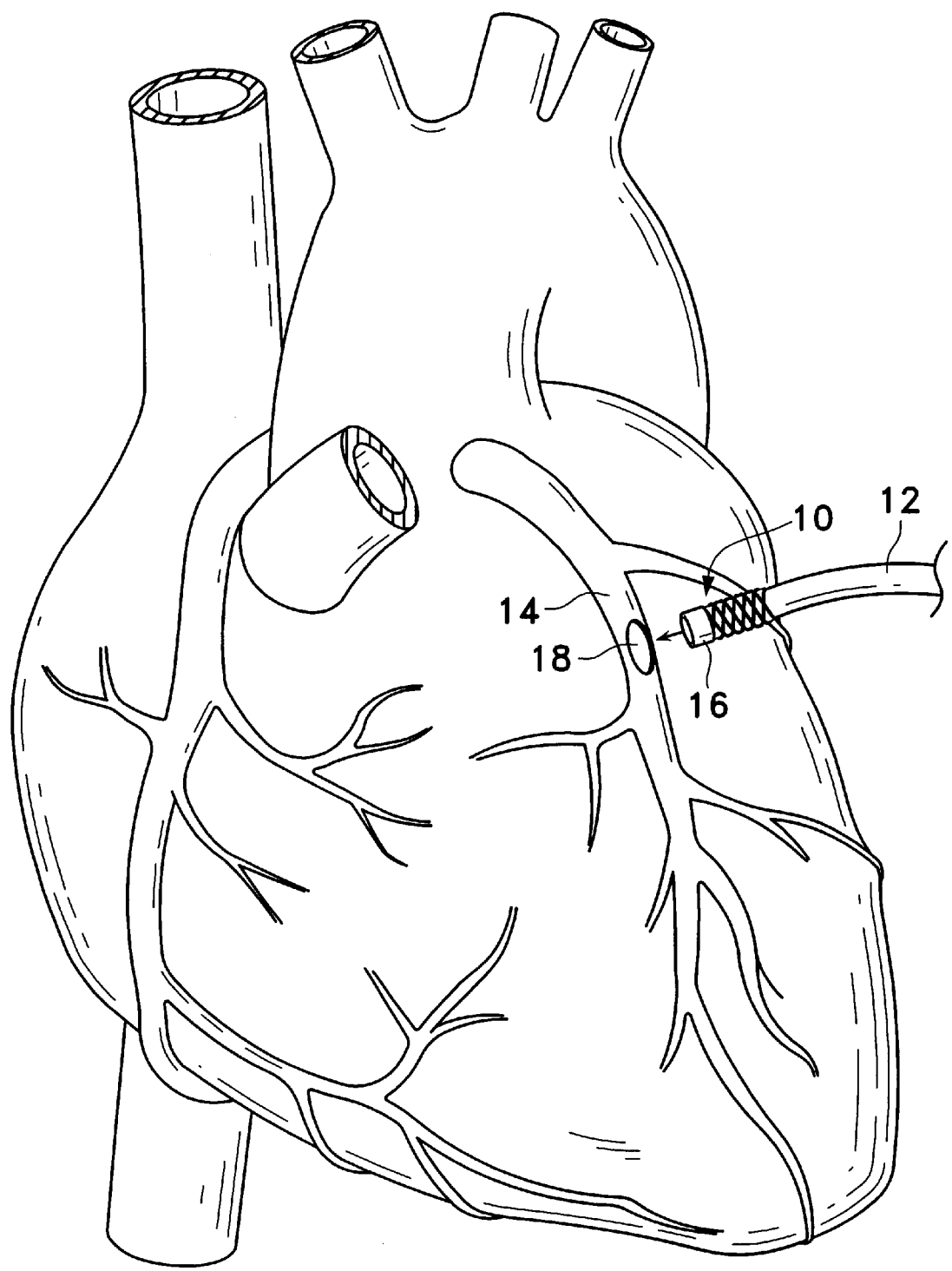
FIG. 2 shows the anastomosis device of FIG. 1 connected to a free end of a graft vessel prior to insertion into an artery.

Referring now to the drawings, and first to FIG. 1, an anastomosis device constructed according to the principles of the present invention is shown and generally indicated with reference numeral 10. The anastomosis device (or fastener) 10 is used to connect a first vessel 12, such as a graft vessel or a thoracic artery to a second vessel 14, such as a coronary artery or vein (FIG. 2). The anastomosis device 10 of the present invention may also be used in connecting various other vessels or arteries and may be used to connect synthetic vascular grafts to an artery.

Figure 7:
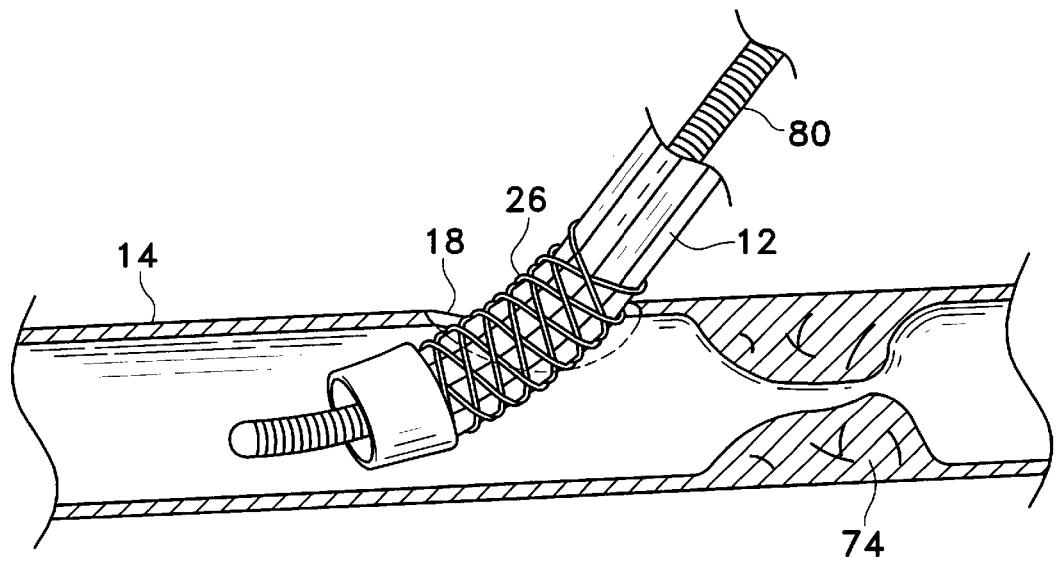
FIG. 7 shows the anastomosis device and balloon catheter being inserted into the artery.

The fastener 10 comprises a tubular member 26. The tubular member 26 may be formed from wire as shown in FIG. 1. The fastener is preferably formed from a mesh material so that the tubular member 26 is sufficiently radially rigid to maintain the fastener 10 in a compressed state, yet flexible enough to be inserted through an opening 18 in the side wall of the graft vessel 12 (FIG. 7). A rigid coil or cage type member may also be used. The tubular member 26 is preferably between about 4 and 12 mm in length, and more preferably between about 5 and 8 mm, for example. The diameter of the fastener 10 in its free state (not compressed or expanded) is preferably between 1 and 6 mm, for example. The tubular member 26 may also have graft material (not shown) attached to it.

Figure 8:
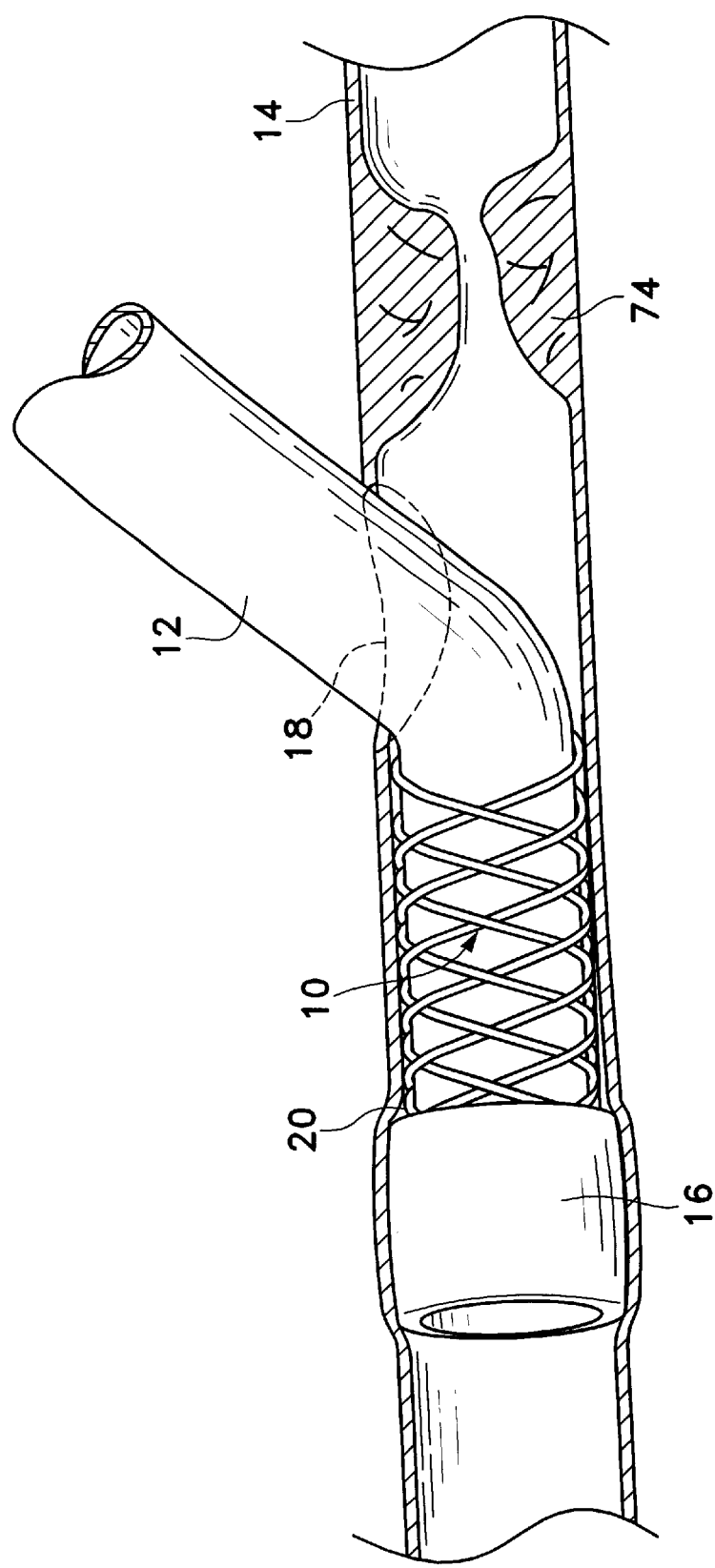
FIG. 8 shows the device of FIG. 1 in a completed anastomosis.

The fastener is radially compressible and expandable so that the fastener is transformable between a compressed state (FIGS. 5A and 5B) and an expanded state (FIG. 8). When used in a distal anastomosis within the coronary artery, for example, the fastener 10 is preferably constructed with the following characteristics. In its compressed state, the fastener 10 is radially compressed to reduce the outer diameter of the fastener to less than about 2 mm. The diameter of the fastener 10 in its compressed state must be smaller than the opening 18 in the side wall of the artery 14 and smaller than the inner diameter of the artery to permit the fastener to be inserted through the opening and moved longitudinally through the artery to be properly positioned (FIG. 7). The tubular member 26 is sufficiently rigid in the axial direction to remain in its compressed state while being inserted into the artery 14 without a sheath or other device radially restraining the fastener. In its expanded state, the outer diameter of the fastener 10 is at least equal to the inner diameter of the artery 14 so that the graft vessel 12 is in sealing engagement with the inner wall of the artery (FIG. 8). The outer diameter of the fastener 10 in its expanded state is approximately 2–4 mm, and is dependent on the inner diameter of the artery 14.

The tubular member 26 may be formed from stainless steel, tantalum, gold, titanium, shape memory alloys such as nitinol, or any other suitable biocompatible material. The tubular member 26 may also be formed from polymeric materials which satisfy the requisite strength and flexibility requirements described above. It is to be understood that other types of tubular members and different sizes of members or materials may be used without departing from the scope of the invention.

Figure 1A:
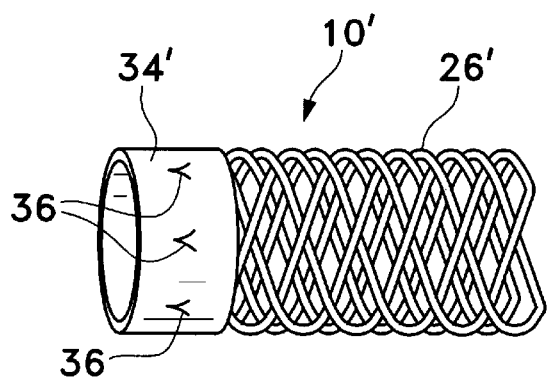
FIG. 1A is an elevated view of the anastomosis device of FIG. 1 with a smooth end margin at one end.

A modified configuration of the anastomosis device 10 of FIG. 1 is shown in FIG. 1A and generally indicated at 10'. The tubular member 26' has an end margin 34' extending from one end thereof. The end margin 34' has a substantially smooth outer surface and may be formed from a continuous piece of metal or any other suitable expandable material. The material is preferably substantially impermeable to blood, to prevent blood from flowing transversely through the end margin 34'. A plurality of barbs 36 extends radially outward from the end margin 34' to securely attach the graft vessel 12 to the fastener 10' (FIG. 3A). The barbs 36 pierce the wall of an everted end 16 of the graft vessel 12 to securely hold the graft vessel in place on the fastener 10. The tubular member 26 may also be formed without the smooth end margin 34', with the barbs 36 connected directly to the member. The barbs 36 may be attached to the tubular member 26' with sutures, thread, or glue, or welded directly to the member, for example. The barbs 36 may also be eliminated and the everted end 16 of the graft vessel 12 may be held in place with biological glue or other suitable adhesive means.

Figure 1B:
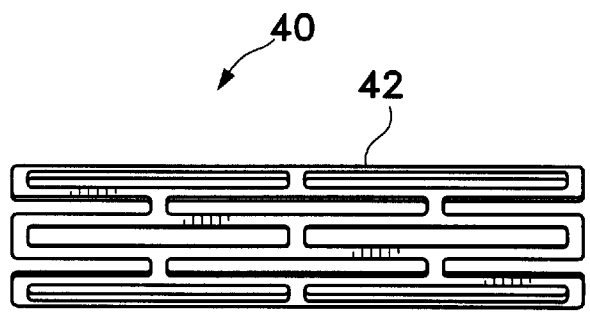
FIG. 1B is an elevated view of a modified configuration of the anastomosis device of FIG. 1.

Another modified configuration of the fastener 10 is shown in FIG. 1B and generally indicated at 40. The fastener 40 comprises a tubular member 42. The tubular member 42 may be made from a stent, generally indicated at 44 (FIG. 9), and further described below. The stent 44 comprises two sections hingedly connected together with a hinge 46. In order to form the fastener 40, the stent 44 is cut in half at the location of the hinge with a suitable cutting instrument. The tubular member 42 preferably has the dimensions and characteristics described above for tubular member 26.

A second embodiment of the present invention is the stent 44 shown in FIG. 9. Instead of cutting the stent 44 into two separate sections, the entire stent (tubular member) is attached to the graft vessel 12 and inserted into the artery 14 as shown in FIG. 10. The length of the stent is preferably between 10 and 20 mm, for example. The stent 44 may be a stent available from Johnson & Johnson Interventional Systems, Inc. Warren, N.J., under model number series PS153 (commonly known as a Palmaz-Schatz stent), for example. An example of the stent 44 is disclosed in U.S. Pat. No. 4,733,665, which is incorporated herein by reference.

The hinge 46 is preferably formed from a flexible strip of metal or any other suitable material. The hinge 46 may also be formed from two or more components (not shown) which cooperate to form a hinge.

Figure 11:
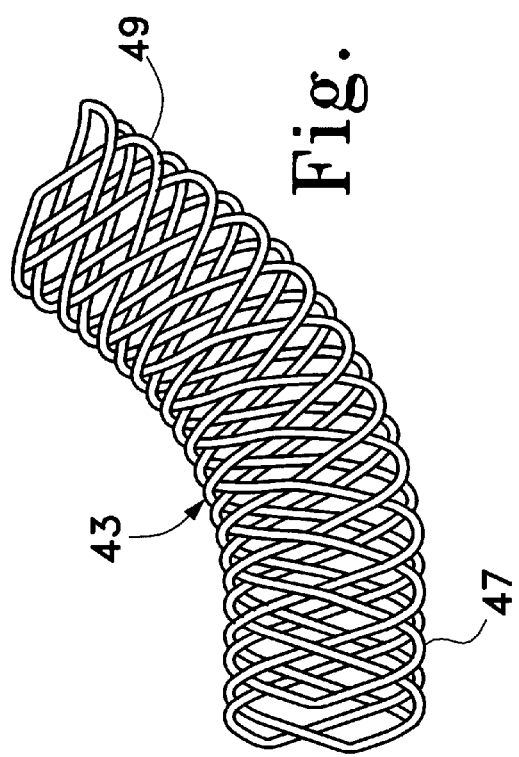
FIG. 11 is an elevated view of a third embodiment of an anastomosis device constructed according to the principles of the present invention.
Figure 12:
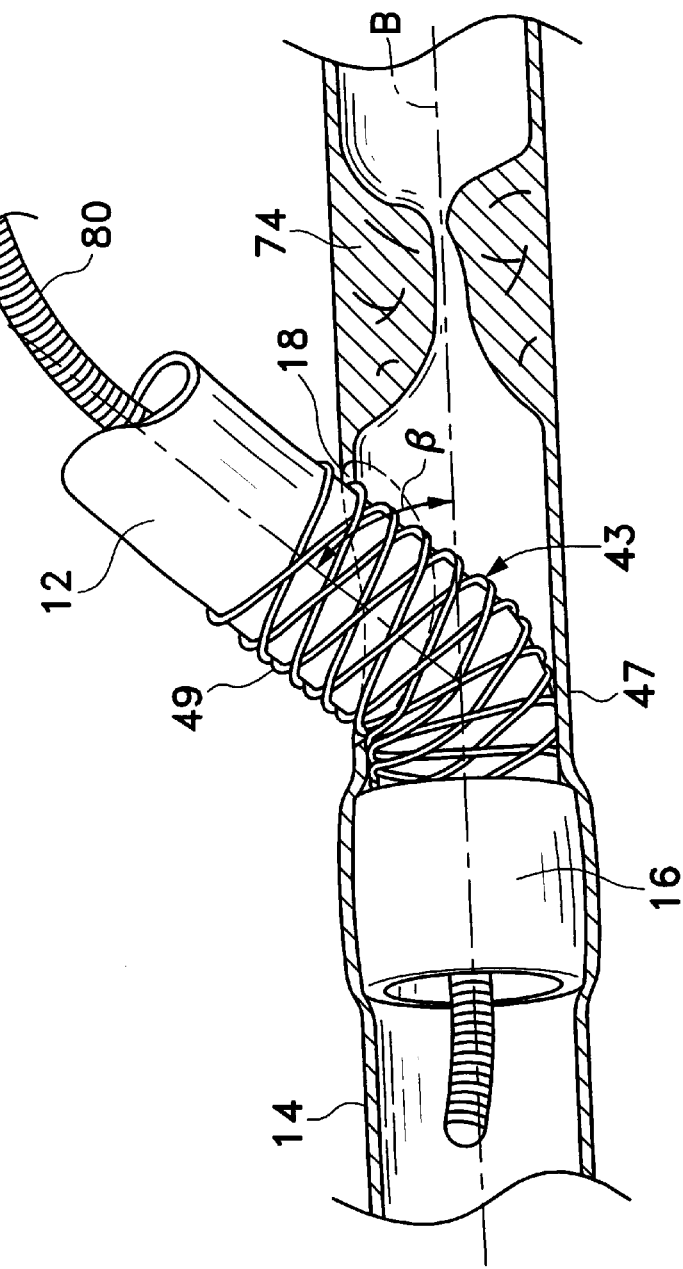
FIG. 12 shows the anastomosis device of FIG. 11 attached to a graft vessel and inserted into an artery with a balloon catheter extending through the graft vessel and device and expanding the device.
Figure 13:
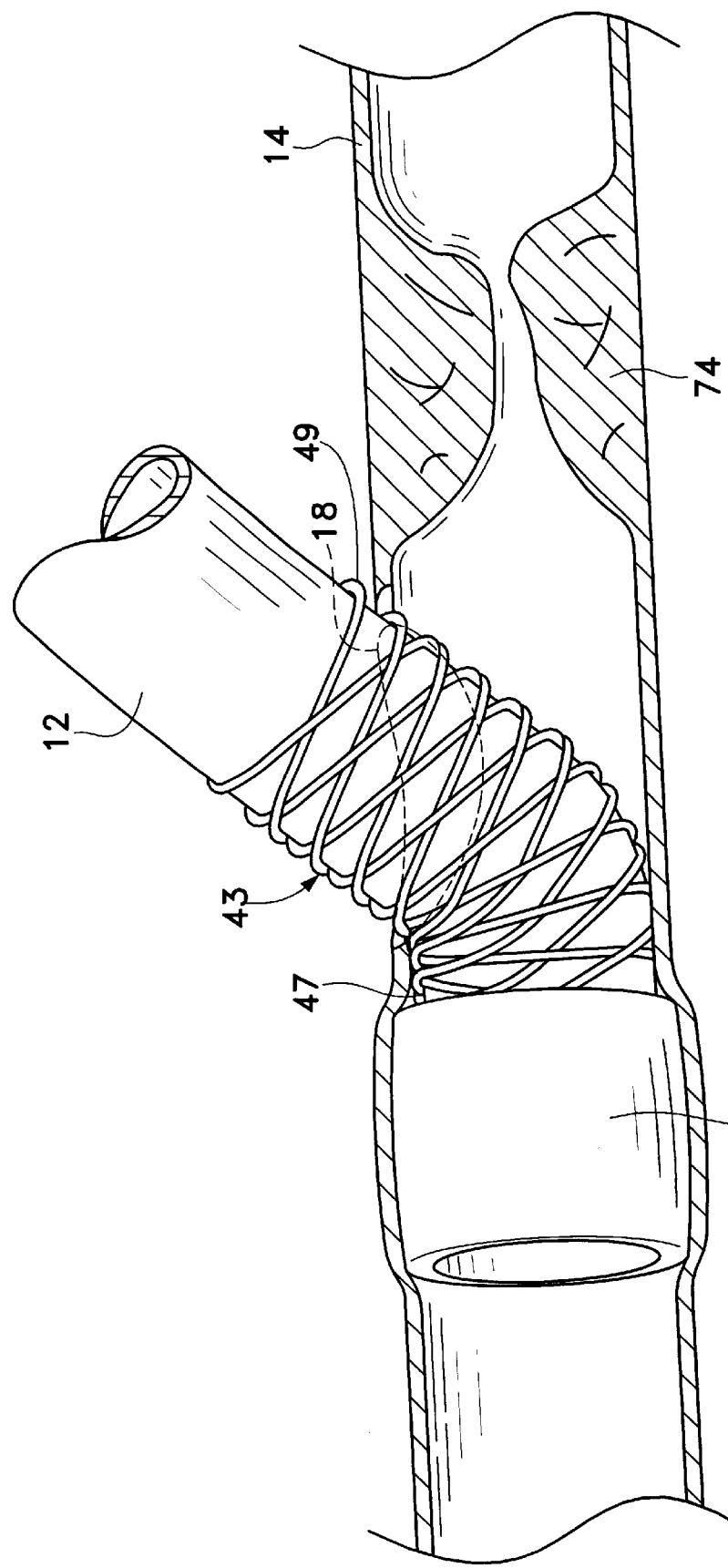
FIG. 13 shows the device of FIG. 11 in a completed anastomosis.

A third embodiment of the present invention is shown in FIG. 11 and generally indicated with reference numeral 43. The fastener 43 comprises a tubular member which is preformed in a bended configuration. The tubular member has a first portion 47 which extends generally straight along a central longitudinal axis B and an angled portion 49 which extends at an angle β of between about 30 and 60 degrees relative to the central longitudinal axis of the first portion. The bent configuration allows the fastener 43 to extend out from the opening 18 in the artery 14 (FIGS. 12 and 13). The fastener 43 thus supports the graft vessel 12 through the arteriotomy to prevent kinking of the graft vessel 12 when the fastener 43 is in its expanded state. A side wall of the tubular member preferably extends substantially around the circumference of the tubular member along its entire length to further prevent kinking. The fastener 43 is preferably formed from stainless steel, tantalum, gold, titanium, shape memory alloys such as nitinol, or any other suitable material which can be formed in a bent configuration and retain its shape. The fastener 43 may also be formed from suitable polymeric materials which can be molded into a bent configuration. The length of the fastener 43 is preferably between 6 and 20 mm, for example.

A fourth embodiment of the present invention is shown in FIG. 14 and generally indicated with reference numeral 50. The fastener 50 comprises a tubular member 51 having a central portion 52 and two end portions 56. The central portion 52 comprises a plurality of struts 58 extending longitudinally between the end portions 56. The struts 58 are preferably formed from a stiff material to prevent the tubular member from buckling in the axial direction. The central portion 52 preferably comprises at least two struts 58 to provide sufficient longitudinal stiffness to the fastener 50. The end portions 56 each comprise an expandable ring formed from a mesh or other suitable materials.

As shown in FIG. 15, an elongated (cylindrical) member 60, formed from a vessel having an outer diameter slightly smaller than the inner diameter of the fastener 50, is inserted through a central longitudinal opening 64 of the fastener. The elongated member 60 is preferably formed from an autograft vessel, taken from the patient's body, but may also be formed from a synthetic vessel made of a suitable biologically inert material. The material of the elongated member 60 is preferably substantially nonporous, with respect to blood, to prevent leakage of the anastomosis. The elongated member 60 is preferably longer than the fastener 50 so that both ends 62 of the elongated member can be everted over the ends of the fastener. The end portions 56 of fastener 50 may have barbs (not shown) extending radially outward therefrom for securing the everted ends 62 of the member to the fastener, as described above for the first embodiment 10. With the elongated member 60 in place, the interior surfaces of the fastener 50 are covered with vascular tissue so that a smooth, continuous, hemocompatible layer is exposed to the bloodstream. This reduces the likelihood of hemolysis or thrombosis due to the presence of foreign material in the bloodstream. The length of the fastener 50 may be 10–17 mm, for example, and is preferably between 13 and 15 mm. The end portions 56 of the fastener 50 each have a length of at least 2 mm, for example, to provide sufficient circumferential surface area for engagement with the inner wall of the artery 14, as described further below.

An opening 68 is formed in a side wall of the elongated member 60 at a location along the central portion 52 of the fastener 50. A free end of the graft vessel 12 is attached to the periphery of the opening 68 by sutures 72, glue, mechanical clips or other suitable means. Alternatively, the free end of the graft vessel may have a large transverse artery or vein branch at its distal end (i.e., the graft vessel has a general T-shaped configuration with a marginal branch vessel at its distal end), in which case the branch can be inserted distally into the opening 68 in the target vessel without the need for additional attachment means. The diameter of the opening 68 in the elongated member 60 is preferably sized to correspond to the diameter of the graft vessel 12 and may be 4–5 mm, for example. A suture pad (not shown) formed in the shape of a ring may be attached to the periphery of the opening 68 in the elongated member 60 to prevent tearing of the member. The pad provides reinforcement to the elongated member 60 and prevents the initiation of tears at the opening 68. The fastener 50 is configured to allow bidirectional flow therethrough. The blood enters the elongated member 60 at the opening 68 therein, and flows out from both ends 56 of the fastener in a direction generally transverse to the direction of the flow entering the elongated member.

Figure 23A:
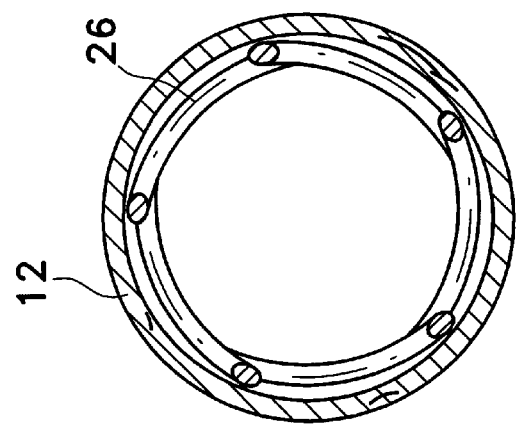
FIG. 23A is a cross-sectional view taken in the plane including line 23A—23A of FIG. 23.
Figure 23:
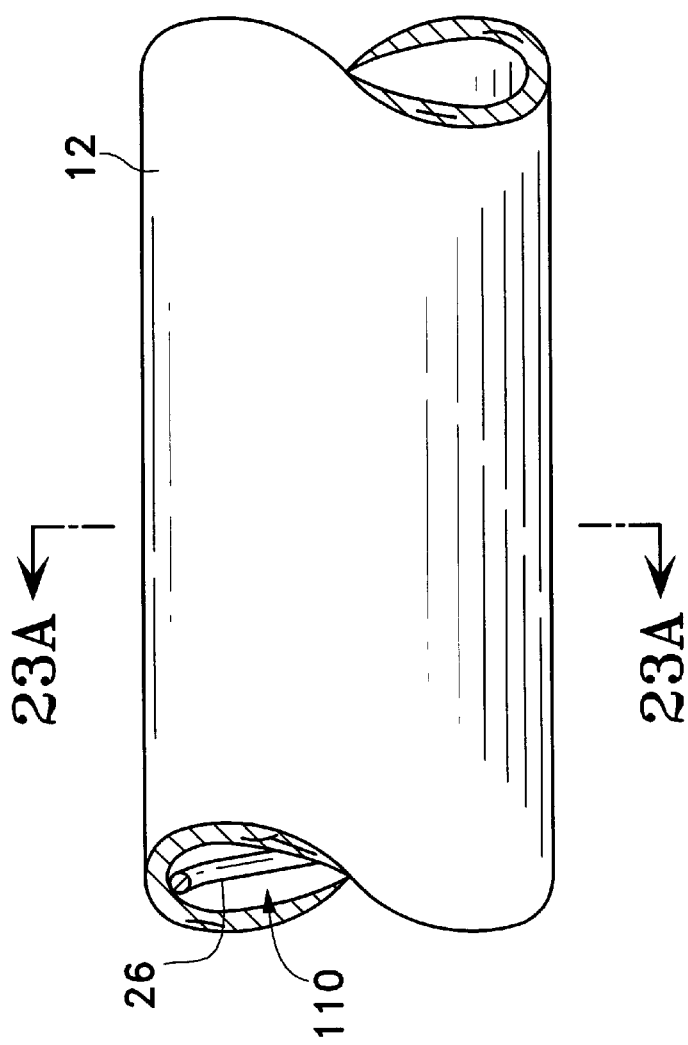
FIG. 23 is an elevated view of a fifth embodiment of an anastomosis device constructed according to the principles of the present invention inserted into a graft vessel.

A fifth embodiment of the anastomosis device of the present invention is shown in FIGS. 23 and 23A and generally indicated at 110. The fastener 110 is similar to the first embodiment 10, except that the tubular member 26 is disposed within the graft vessel 12 rather than over the vessel. The member 26 is compressed to have an outer diameter smaller than the inner diameter of the vessel 12 and then inserted longitudinally into the vessel 12. The member 26 may be attached to the vessel 12 by sutures or other suitable attachment means (not shown). Instead of using attachment means, the tubular member 26 may be slightly expanded to engage the inner wall of the graft vessel 12 to hold the member in place within the vessel. The tubular member 26 may be expanded with a balloon catheter, for example. The fastener 110 can be completely enclosed by the graft vessel 12 as shown, or can extend a short distance from the end of the graft vessel.

FIG. 2 shows an exemplary use of the anastomosis device 10 of the present invention in an open surgical coronary artery bypass graft procedure to create a distal anastomosis. The left internal thoracic artery is used as the graft vessel 12. In this example, the left anterior descending artery 14 contains a blockage or narrowing 74. If left untreated, this diseased artery may lead to insufficient blood flow and eventual angina, ischemia, and possibly myocardial infarction.

Conventional coronary bypass graft procedures require that a source of arterial blood be prepared for subsequent bypass connection to the diseased artery. An arterial graft may be used to provide a source of blood flow, or a free graft may be used and connected at the proximal end to a source of blood flow. Preferably, the source of blood flow is one of any number of existing arteries that are dissected in preparation for the bypass graft procedure. In many instances it is preferred to use either the left or right internal thoracic artery. Other vessels which may be used include the saphenous vein, gastroepiploic artery in the abdomen, radial artery, and other arteries harvested from the patient's body as well as synthetic graft materials, such as Dacron or Goretex grafts. If a free graft vessel is used, the upstream end of the dissected vessel, which is the arterial blood source, will be secured to the aorta to provide the desired bypass blood flow, as is well known by those skilled in the art. It is to be understood that the anastomosis device of the present invention may be used in other vessel anastomoses.

Figure 3:
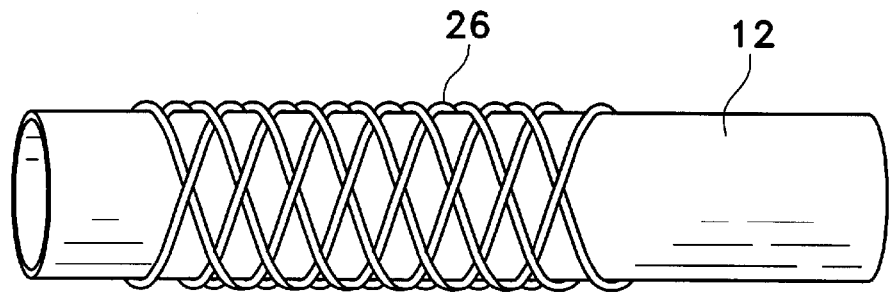
FIG. 3 is an elevated view of the anastomosis device of FIG. 1 with the graft vessel inserted therein.
Figure 3A:
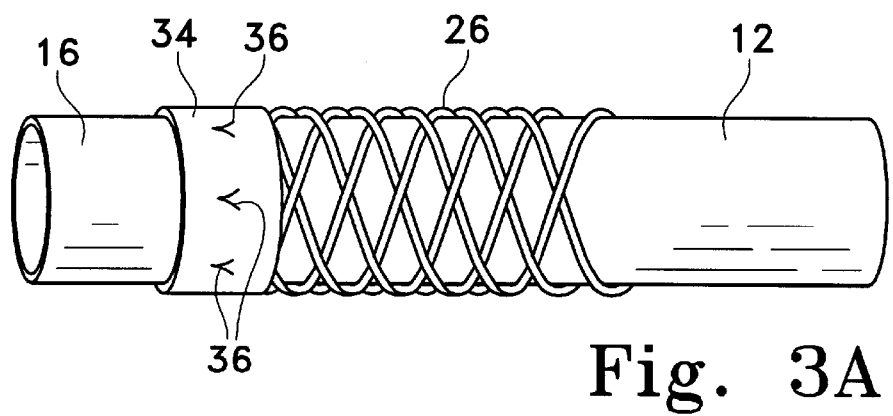
FIG. 3A is an elevated view of the anastomosis device of FIG. 1A with the graft vessel inserted therein.
Figure 4:
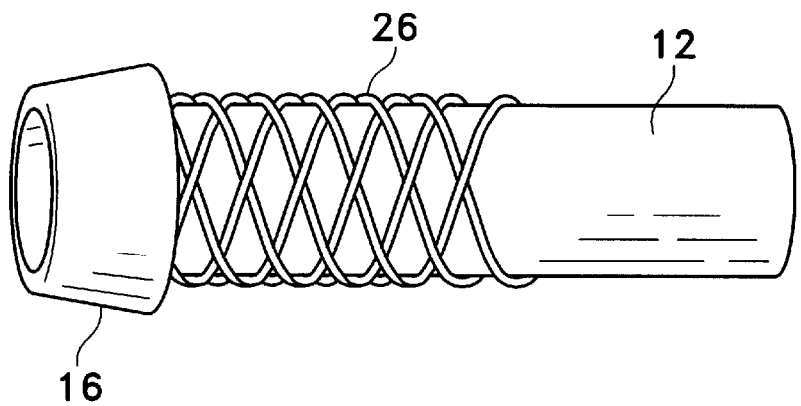
FIG. 4 is an elevated view of the anastomosis device of FIG. 3 with a free end of the graft vessel everted over an end of the device.

In order to perform an anastomosis with the fasteners 10, 10', 40 of the first embodiment, or the fasteners 44, 43, of the second and third embodiments, respectively, the graft vessel 12 is first inserted into the device with an insertion tool (not shown) as is well known by those skilled in the art (FIG. 3). The following example refers generally to fastener 10, but applies to the other fasteners of the first embodiment except where noted. The graft vessel 12 is pulled through the fastener 10 until the graft vessel extends a short distance from one end of the device. The free end 16 of the graft vessel 12 is then everted over the end of the fastener 10 (FIGS. 3 and 4). The free end may also be placed over the barbs 36 extending from the end margin 34' of the fastener 10' (FIG. 3A). The barbs 36 partially penetrate the wall of the graft vessel 12 to securely hold the vessel in place on the fastener 10'.

Figure 5A:
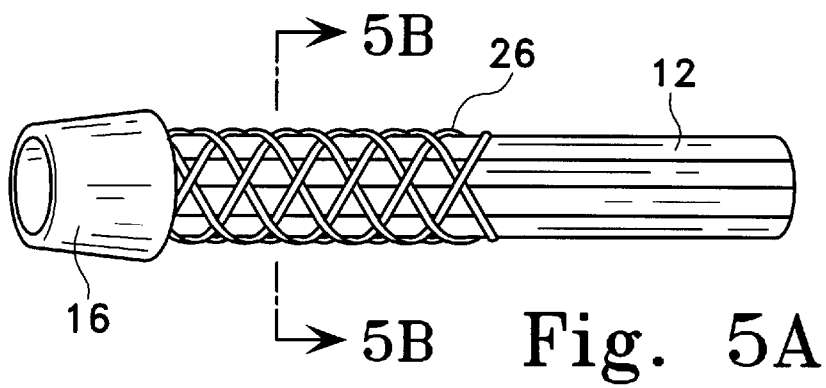
FIG. 5A is an elevated view of the anastomosis device of FIG. 4 shown in a compressed state for insertion into the artery.
Figure 5B:
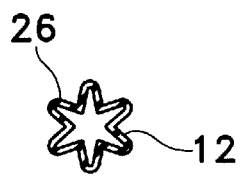
FIG. 5B is a cross-sectional view taken in the plane including line 5B—5B of FIG. 5A.
Figure 6:
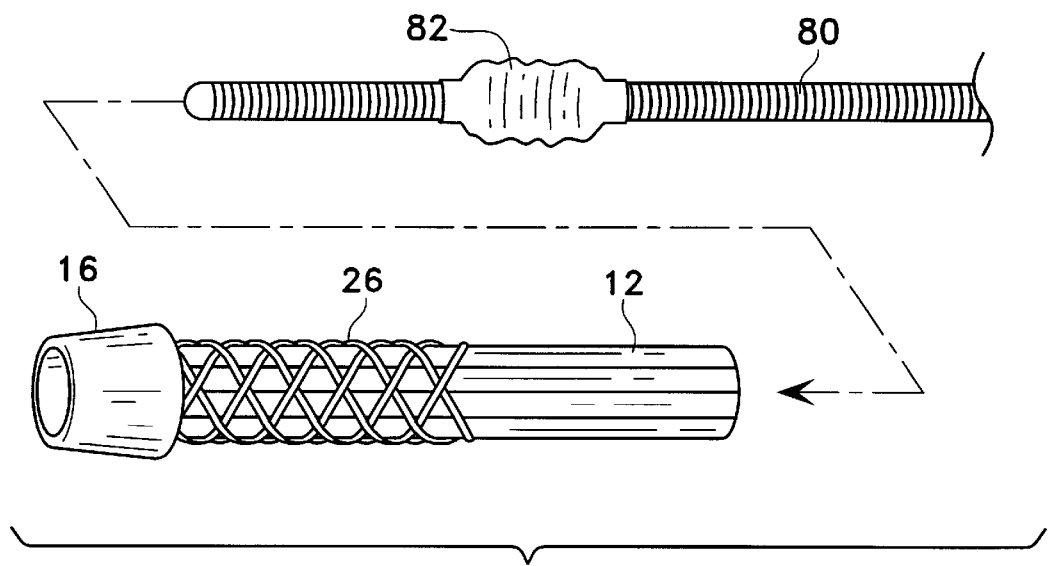
FIG. 6 shows a balloon catheter ready for insertion into the device of FIG. 5.

After attaching the graft vessel 12 to the fastener 10, the fastener is radially compressed to reduce the outer diameter of the fastener (FIGS. 5A and 5B). The diameter is reduced sufficiently to allow the fastener 10 to move longitudinally within the artery 14. A balloon catheter 80 having at least one balloon 82, is inserted through the lumen of the vessel 12 and fastener 10 to expand the end portion 20 of the fastener for engagement with an inner wall of the artery 14 (or vein) (FIG. 6). A slit, approximately 5–10 mm in length is formed in a side wall of the artery 14 with a scalpel or other appropriate cutting instrument. Alternatively, a circular or oval punch may be used to facilitate the arteriotomy. The fastener 10 is then inserted into the opening 18 formed in the vessel (FIG. 7). The fastener 10 is positioned within the artery 14 so that the end portion 20 of the fastener extends generally coaxial with the artery. The fastener 43 is preferably positioned in the artery 14 such that the majority of the fastener is disposed within the artery (e.g., approximately 80 percent of the fastener is located within the artery) (FIG. 13). The balloon 82 is inflated to radially expand the end portion 20 of the fastener 10 so that the graft vessel 12 sealingly engages an inner wall of the artery 14 to secure the fastener within the artery, and prevent leakage of blood between the everted end 16 of the vessel 12 and the inner wall of the artery (FIG. 8). The engagement of the graft vessel 12 with the inner wall of the artery 14 prevents substantial longitudinal movement of the fastener within the artery. The balloon 82 is deflated and the catheter 80 is withdrawn from the graft vessel. The vessel 12 is now coupled with the artery 14 and the anastomosis is complete. If necessary, a biological glue may be coated to the everted surface of the graft vessel to facilitate a fluid-tight seal.

The following example is provided for purposes of illustration and is not intended to limit the invention. Anastomoses were created on cadaver hearts with a fastener constructed as shown in FIG. 1B. The fastener was formed by cutting a stent as shown in FIG. 9 in half. The left internal thoracic artery or saphenous vein were harvested and passed through the length of the fasteners so that a 2 mm to 3 mm cuff extended beyond the end of the fasteners. The cuff was everted around the end of the fastener (FIG. 4). The fastener was then compressed around an angioplasty balloon catheter. A 7–10 mm arteriotomy was performed and the fastener was inserted through the arteriotomy into the coronary artery about 75% to 100% the length of the fastener. The balloon was inflated to 14 atmospheres for 30 seconds. The balloon was then deflated and the catheter was removed, leaving the fastener within the coronary artery. Colored saline was injected into the internal thoracic artery and saphenous vein grafts under high pressure (in excess of 300 mm Hg). In two of nine instances leaks were observed. In one case, the fastener was not seated deeply enough within the coronary vessel (>25% of the length of the fastener). In one additional cadaver, a biologic glue was applied around the everted surface of the graft. In the four instances in which it was tried, no leaks were observed around the fastener.

In order to insert the fastener 50 of the fourth embodiment, a vessel is provided for use as the elongated member 60 (FIG. 15). The elongated member 60 is inserted through the longitudinal opening 64 in the tubular member and the ends 62 of the vessel 60 are everted over the tubular member. An opening 68, having a diameter of approximately 4–5 mm is formed in the side wall of the elongated member 60. A reinforcement ring or suture pad (not shown) may be attached to the periphery of the opening 68 in the side wall of the elongated member 60. The graft vessel 12 is then attached to the tubular member at the location of the opening 68 in the side wall of the elongated member 60 (FIG. 16). A balloon catheter 90, preferably having three balloons 92, 94, 96, is inserted into the artery 14 (FIG. 17). The upstream balloon 92 (balloon farthest to the right as viewed in FIG. 17) is inflated to function as an occlusion catheter and block the flow of blood at the location of the anastomosis. Blood is supplied downstream of the anastomosis through openings 98 located on the end of the catheter 90. The two downstream balloons 94, 96 may be combined into a single cylindrical balloon (not shown) having a length approximately equal to the length of the fastener 50.

Figure 20:
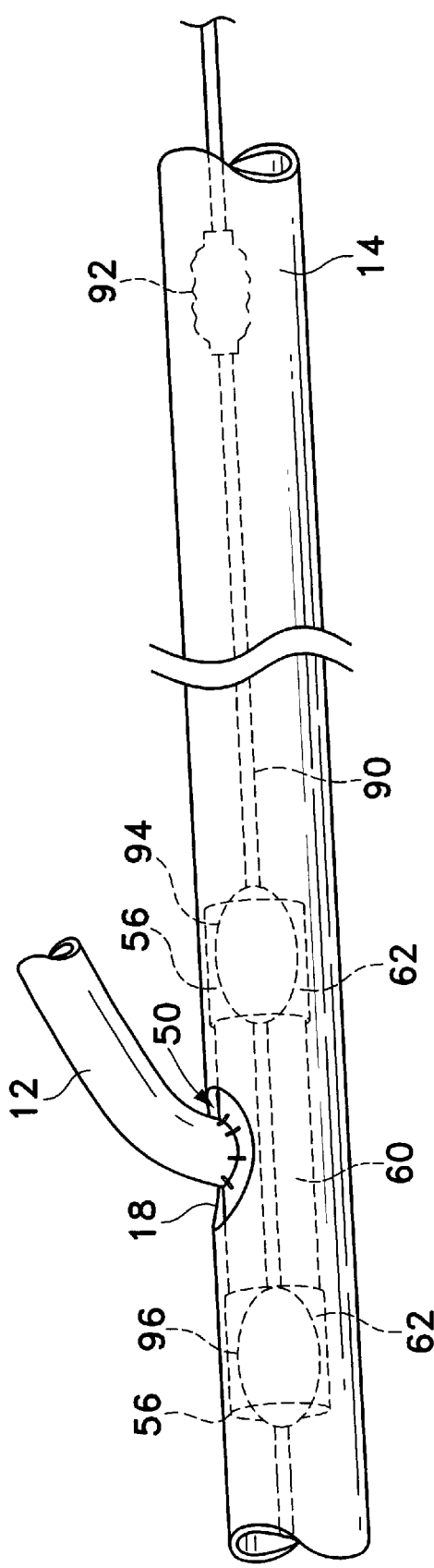
FIG. 20 shows the device and balloon catheter of FIG. 19 positioned within the artery.
Figure 21:
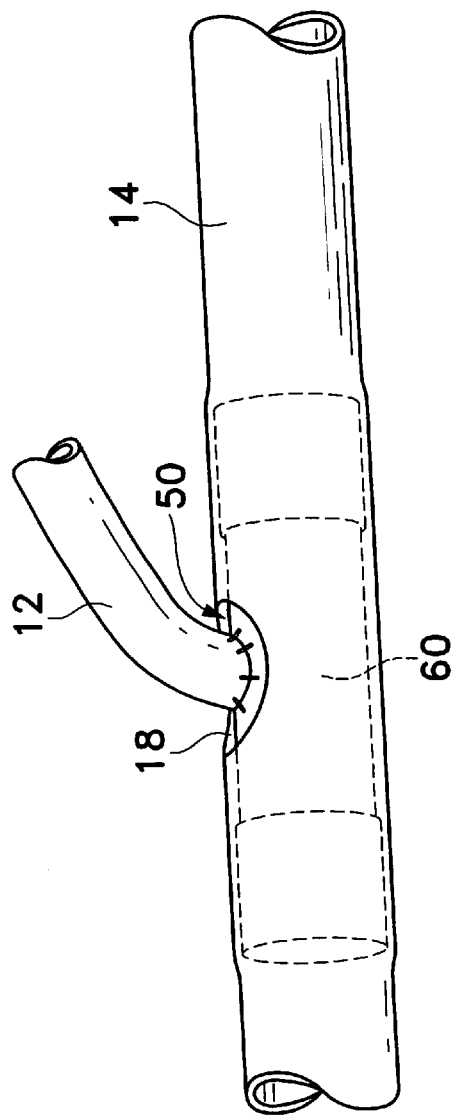
FIG. 21 shows the completed anastomosis.

A slit, approximately 10–15 mm in length is formed in the side wall of the artery 14 at a location between two of the balloons located at the end of the catheter to form the opening 18 (FIG. 18). The downstream end of the catheter 90 is pulled through the opening 18 in the side wall of the artery 14 and inserted through the fastener 50 (FIG. 19). The fastener 50 and catheter 90 are then inserted through the opening 18 into the artery 14 with the fastener extending generally longitudinally along the artery and the graft vessel 12 extending through the opening generally transversely to the fastener (FIG. 20). In the alternative, the catheter 90 can remain in the artery 14 while the fastener 50 is inserted into the artery and placed over the catheter. The fastener 50 is positioned so that the graft vessel 12 extends through generally the center of the opening 18 and the end portions 56 of the fastener are located on opposite sides of the opening. The two downstream balloons 94, 96 are inflated and the end portions 56 are expanded to engage the inner walls of the artery 14. The balloons 92, 94, 96 are then deflated and the catheter 90 is removed from the artery 14 to form the completed anastomosis (FIG. 21).

The fastener 110 of the fifth embodiment (FIG. 23) is inserted into the second vessel as described above for the first embodiment, after insertion of the fastener into the graft vessel 12.

Figure 22:
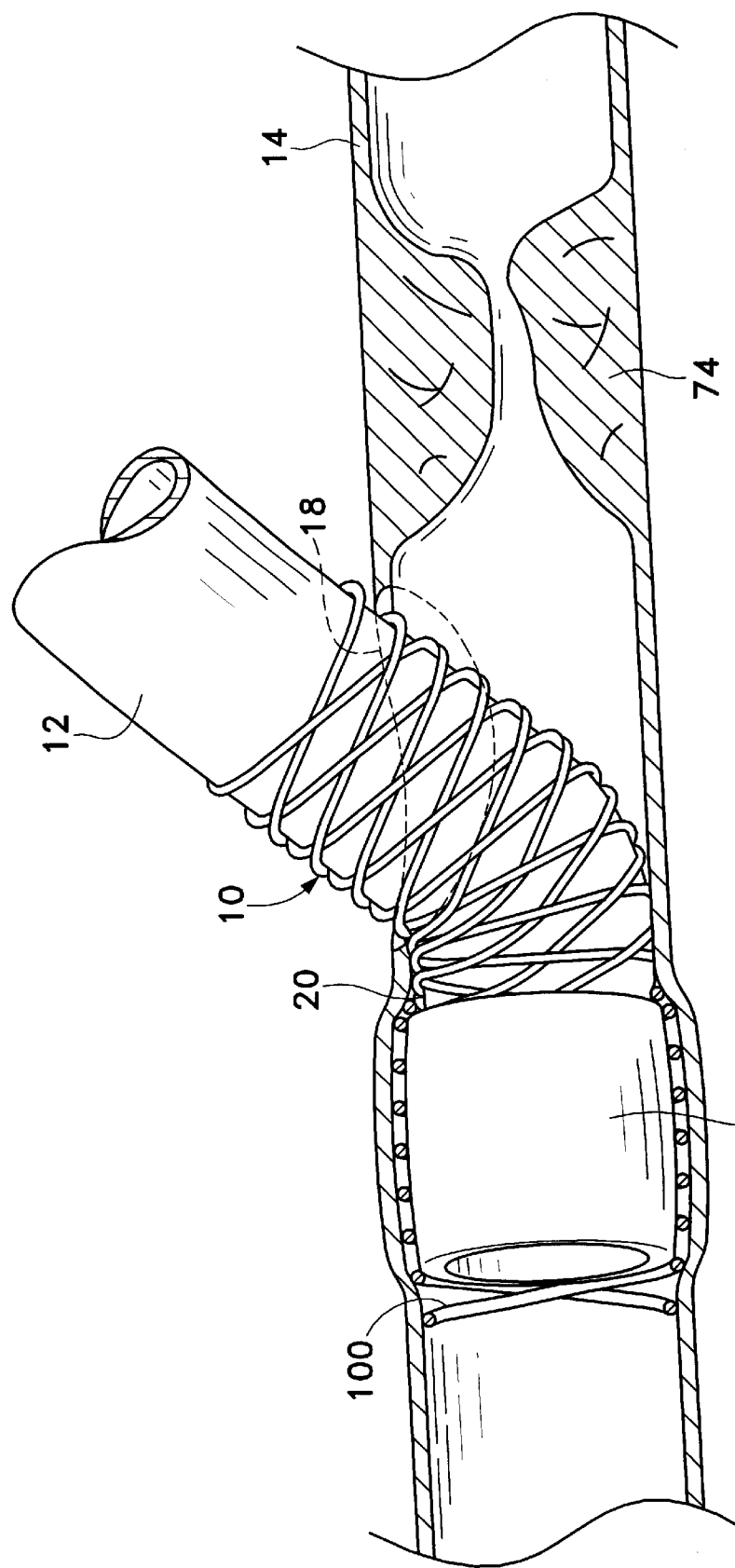
FIG. 22 shows an insert interposed between the artery and the device of FIG. 11.

A second insert 100 may also be inserted into the artery and expanded to dilate the artery 14 prior to inserting the fastener of the first 10, 10', 40, second 44, third 43, fourth 50, or fifth 110 embodiments. Use of an insert with fastener 43 is shown in FIG. 22. The insert 100 is inserted into the artery 14 at a location where the portion of the fastener 43 to be expanded will be located. The fastener 43 is then inserted into the artery 14 and insert 100, and expanded. Two inserts 100 may similarly be inserted into the artery 14 at the locations where each end of the fastener will be placed for fastener 50. The insert 100 may be formed of a mesh material as described above.

The anastomosis devices may also be expanded without the use of balloons. For example, the tubular member may be formed of a shape memory alloy such as nitinol, as is well known by those skilled in the art. After the fastener is attached to the graft vessel 12, the tubular member is cooled and reshaped to a compressed form. The fastener is then inserted into an insulated sheath (not shown) to maintain the temperature of the tubular member below its transformation temperature. The sheath is then inserted and properly positioned within the artery 14. The sheath is removed and the tubular member is permitted to be warmed above its transformation point and urged against the inner wall of the artery 14.

If required, cardiac stabilization such as described in co-pending provisional patent application, Ser. No. 60/055,127, for Compositions, Apparatus and Methods For Facilitating Surgical Procedures, filed Aug. 8, 1997 and invented by Francis G. Duhaylongsod, MD., may be used during the procedure. Other pharmacological or mechanical methods may also be used.

The anastomosis devices of the first, second, third and fifth embodiments may be supplied alone or with a prosthetic graft vessel already attached to the fastener. The anastomosis device 50 of the fourth embodiment may be supplied as a tubular member by itself, a tubular member with the elongated member 60 already inserted, or a tubular member with the elongated member inserted and a prosthetic graft vessel attached to the elongated member.

It will be observed from the foregoing that the anastomosis devices of the present invention have numerous advantages. Importantly, the devices require a minimal amount of manipulation and can be quickly installed. The devices have very few parts and are non-complex, thus simplifying attachment of the device to the vessels. The risk of thrombosis is reduced by substantially eliminating exposure of the blood flow to foreign material. Furthermore, the devices enlarge the diameter of the artery 14, thus increasing the cross-sectional area of the blood flow passage, rather than reducing the diameter of the passage, as is common with prior art devices.

All references cited above are hereby incorporated herein by reference.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A method of coupling a first vessel and a second vessel in an anastomosis, the method comprising the steps of:
   providing a first vessel with a fastener coupled thereto;
   inserting at least a portion of the fastener into an opening formed in a side wall of the second vessel with an end portion of the fastener extending generally longitudinally within the second vessel; and
   radially expanding the at least a portion of the fastener to expand the first vessel to sealingly secure the first vessel about a perimeter of an inner wall of the second vessel.

2. The method of claim 1 wherein the step of radially expanding the at least a portion of the fastener comprises inflating a balloon of a balloon catheter located within the fastener.

3. The method of claim 1 further comprising radially compressing the fastener so that the fastener has an outer diameter smaller than the opening in the side wall of the second vessel, prior to inserting the fastener into the second vessel.

4. The method of claim 1 wherein the step of providing a first vessel with a fastener coupled thereto comprises attaching the first vessel to the fastener coaxial with the fastener.

5. The method of claim 4 wherein the step of attaching the first vessel to the fastener comprises inserting a free end of the first vessel longitudinally through an opening in the fastener and everting the end of the first vessel over one end of the fastener.

6. The method of claim 1 further comprising the steps of inserting a balloon catheter having at least one balloon into the first vessel and fastener with the balloon being deflated, and inflating the balloon to engage at least a portion of the fastener with an inner wall of the second vessel.

7. The method of claim 1 further comprising inserting an insert longitudinally into the second vessel prior to inserting the fastener into the second vessel, the fastener being inserted into the insert.

8. The method of claim 1 wherein the step of providing a first vessel with a fastener coupled thereto includes attaching a free end of the first vessel to the periphery of an opening formed in a side wall of the fastener.

9. The method of claim 8 wherein the step of attaching the first vessel to the fastener comprises suturing the free end of the first vessel to the fastener.

10. The method of claim 5 wherein the step of attaching the first vessel to the fastener comprises using one or more mechanical clips.

11. The method of claim 5 wherein the step of attaching the first vessel to the fastener comprises attaching the first vessel to the fastener with biological glue.

12. The method of claim 9 further comprising inserting a balloon catheter having at least two balloons into the second vessel.

13. The method of claim 9 further comprising inserting a balloon catheter having at least three balloons into the second vessel.

14. The method of vlaim 13 further comprising the steps of forming an opening in a side wall of the second vessel, inserting the balloon catheter into the fastener with two of the balloons positioned at opposite end of the fastener, and inserting the fastener into the second vessel.

15. The method of claim 1 further comprising the steps of cooling the fastener to radially compress the fastener and inserting the fastener into an insulated sheath prior to insertion of the fastener into the second vessel.

16. The method of claim 15 wherein the step of radially expanding comprises removing the sheath to allow the fastener to warm and radially expand.

17. The method of claim 1 further comprising bending the fastener so that a portion of the fastener extends out from the opening in the side wall of the second vessel.

18. A method of coupling a first vessel and a second vessel in an anastomosis, the method comprising the steps of:
   positioning a fastener comprising a tubular member longitudinally within an opening in a free end portion of the first vessel;
   inserting the free end portion of the first vessel into an opening formed in a side wall of the second vessel with an end portion of the fastener extending generally longitudinally within the second vessel; and
   radially expanding at least a portion of the fastener to expand the first vessel to sealingly secure the first vessel about a perimeter of an inner wall of the second vessel.

19. A method of coupling a first vessel and a second vessel in an anastomosis, the method comprising the steps of:

providing a first vessel with a fastener coupled thereto;

inserting at least a portion of the fastener into an opening formed in a side wall of the second vessel with an end portion of the fastener extending generally longitudinally within the second vessel and a portion of the first vessel extending longitudinally within the second vessel; and radially expanding at least a portion of the fastener to sealingly secure the first vessel to an inner wall of the second vessel.

20. A method of coupling a first vessel and a second vessel in an anastomosis, the method comprising the steps of:

positioning a fastener comprising a tubular member longitudinally within an opening in a free end portion of the first vessel;

inserting the free end portion of the first vessel into an opening formed in a side wall of the second vessel with an end portion of the fastener extending generally longitudinally within the second vessel and a portion of the first vessel extending longitudinally within the second vessel; and radially expanding at least a portion of the fastener to sealingly secure the first vessel to the second vessel.

* * * * *